(12) United States Patent
Chinta et al.

(10) Patent No.: US 8,785,706 B2
(45) Date of Patent: Jul. 22, 2014

(54) ADDITION OF A BASE TO ENHANCE PRODUCT YIELD IN ALKYLATION REACTIONS

(75) Inventors: Sivadinarayana Chinta, Missouri City, TX (US); Joseph L. Thorman, Milwaukee, WI (US)

(73) Assignee: Fina Technology, Inc., Houston, TX (US)

( * ) Notice: Subject to any disclaimer, the term of this patent is extended or adjusted under 35 U.S.C. 154(b) by 179 days.

(21) Appl. No.: 13/457,508

(22) Filed: Apr. 27, 2012

(65) Prior Publication Data

US 2012/0296141 A1 Nov. 22, 2012

Related U.S. Application Data

(60) Provisional application No. 61/488,782, filed on May 22, 2011.

(51) Int. Cl.
*C07C 15/073* (2006.01)
*C07C 15/46* (2006.01)

(52) U.S. Cl.
USPC .......................................... 585/467; 585/469

(58) Field of Classification Search
CPC ........ C07C 2/867; C07C 2/865; C07C 2/864; C07C 15/073; C07C 15/46; C07C 2529/06
USPC .................................................. 585/467, 469
See application file for complete search history.

(56) References Cited

U.S. PATENT DOCUMENTS

| | | | |
|---|---|---|---|
| 4,463,204 A * | 7/1984 | Liu | ............................... 585/437 |
| 4,483,936 A | 11/1984 | Liu et al. | |
| 4,483,937 A | 11/1984 | Liu et al. | |
| 5,243,115 A | 9/1993 | Smith, Jr. et al. | |
| 2008/0058566 A1 | 3/2008 | Butler et al. | |
| 2010/0041931 A1 | 2/2010 | Pelati et al. | |

\* cited by examiner

*Primary Examiner* — Thuan D Dang

(57) ABSTRACT

A process for making styrene including providing toluene, a co-feed, and a $C_1$ source to a reactor containing a catalyst having acid sites and reacting toluene with the $C_1$ source in the presence of the catalyst and the co-feed to form a product stream containing ethylbenzene and styrene, wherein the $C_1$ source is selected from methanol, formaldehyde, formalin, trioxane, methylformcel, paraformaldehyde, methylal, dimethyl ether, and wherein the co-feed removes at least a portion of the acid sites on the catalyst. The co-feed can be selected from the group of aniline, amines, cresol, anisol, and combinations thereof.

11 Claims, 2 Drawing Sheets

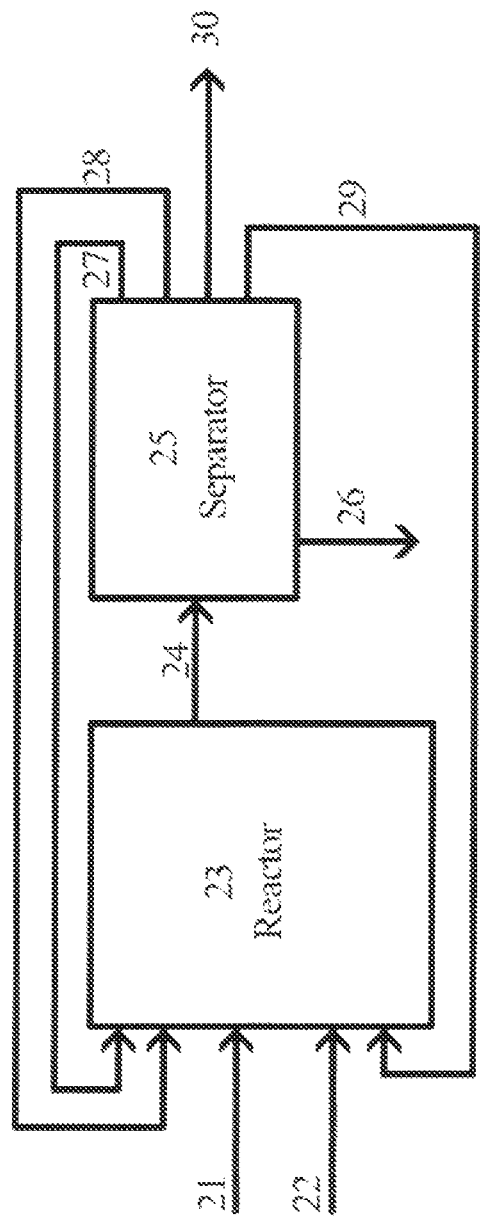

ADDITION OF A BASE TO ENHANCE PRODUCT YIELD IN ALKYLATION REACTIONS

CROSS-REFERENCE TO RELATED APPLICATIONS

This application claims priority to U.S. Provisional Patent No. 61/488,782 filed on May 22, 2011.

FIELD

The present invention generally relates to catalysts, including zeolites, for alkylation and other reactions. More specifically, the present invention relates to catalysts for the alkylation reactions of toluene with methanol and/or formaldehyde.

BACKGROUND

A zeolite is a crystalline alumino-silicate that is well known for its utility in several applications. Zeolites have been used in dealkylation, transalkylation, isomerization, cracking, disproportionation, and dewaxing processes, among others. Its well-ordered structure is composed of tetrahedral $AlO_4^{-4}$ and $SiO_4^{-4}$ molecules bound by oxygen atoms that form a system of pores typically on the order of 3 Å to 10 Å in diameter. These pores create a high internal surface area and allow the zeolite to selectively adsorb certain molecules while excluding others, based on the shape and size of the molecules. Thus, a zeolite can be categorized as a molecular sieve. A zeolite can also be termed a "shape selective catalyst." The small pores of the zeolite can restrict reactions to certain transition states or certain products, preventing shapes that do not fit the contours or dimensions of the pores.

The pores of a zeolite are generally occupied by water molecules and cations. Cations balance out the negative charge caused by trivalent aluminum cations which are coordinated tetrahedrally by oxygen anions. A zeolite can exchange its native cations for other cations; one example is the exchange of sodium ions for ammonium ions. In some ion-exchanged forms, such as the hydrogen form of a zeolite, the catalyst is strongly acidic. These acidic active sites may be useful for alkylation as well as many other reactions. For instance, zeolites can serve as a catalyst for Friedel-Crafts alkylations, replacing traditional aluminum trichloride and other liquid acid catalysts that can be corrosive and damaging to the reactor.

One alkylation reaction for which zeolite can be used as a catalyst is the alkylation of toluene with methanol and/or formaldehyde to form styrene. Styrene, also known as vinyl benzene, is an organic compound having the chemical formula $C_6H_5CHCH_2$. The monomer styrene may be polymerized to form the polymer polystyrene. Polystyrene is a plastic that can form many useful products, including molded products and foamed products, all of which increase the need for production of styrene.

In the production of styrene, zeolite catalysts may be utilized. The zeolite used in the production of styrene can be categorized as a heterogeneous acid catalyst. The zeolite is characterized as heterogeneous because it is in a different phase than the reactants. The zeolite catalyst is solid and usually supported by an alumina or silica binder to increase its mechanical stability inside the reactor bed.

Bulk zeolitic catalysts typically contain an abundance of acid sites. In the presence of alkylation reactions, however, these acid sites may contribute to the production of unwanted by-products, such as xylenes.

Therefore, it would be desirable to reduce the amount of the acid sites on a zeolitic catalyst used in the production of styrene. It would also be desirable to use an alkylation catalyst capable of increasing the selectivity to styrene.

SUMMARY

The present invention in its many embodiments relates to a process of making styrene. In an embodiment of the present invention, a process is provided for making styrene including providing toluene, a co-feed, and a $C_1$ source to a reactor including a catalyst containing acid sites and reacting toluene with the $C_1$ source in the presence of the catalyst and the co-feed to form a product stream including ethylbenzene and styrene. The co-feed is a base compound that reduces the number of active acid sites on the catalyst.

In an embodiment, either by itself or in combination with any other embodiment, the $C_1$ source can be selected from the group of methanol, formaldehyde, formalin, trioxane, methylformcel, paraformaldehyde, methylal, dimethyl ether, and combinations thereof. The toluene conversion can be at least 3 mol %. The selectivity to styrene can be at least 10 mol % and the selectivity to ethylbenzene can be at least 10 mol %.

In an embodiment, either by itself or in combination with any other embodiment, catalyst comprises at least one promoter on a support material that can be selected from the group of Co, Mn, Ti, Zr, V, Nb, K, Cs, Ga, B, P, Rb, Ag, Na, Cu, Mg, Fe, Mo, Ce, and combinations thereof.

In an embodiment, either by itself or in combination with any other embodiment, the co-feed adds basic sites to the catalyst. Optionally, the co-feed removes at least a portion of the total number of active acid sites on the catalyst by the molecules of the co-feed occupying spatial volume near the acid sites of the catalyst. The co-feed can be added to the catalyst prior to the toluene and the C1 source. Optionally, the co-feed can be simultaneously fed to the reactor with the toluene and the C1 source. The co-feed can be selected from the group of aniline, amines, cresol, anisol, and combinations thereof. The co-feed can be present in amounts of from 0.1 to 5.0 wt % based on the total weight of the feed. Optionally, the co-feed is present in amounts of from 0.5 to 1.0 wt % based on the total weight of the feed.

Another embodiment of the present invention includes a method of preparing a catalyst. The method includes providing a substrate and a first solution including at least one promoter; contacting the substrate with the first solution; obtaining a catalyst including at least one promoter and having an initial number of active acid sites; placing the catalyst in an alkylation reactor; and contacting the catalyst in the alkylation reactor with a co-feed selected from the group of aniline, amines, cresol, anisol, and combinations thereof. The co-feed reduces the number of active acid sites.

In an embodiment, either by itself or in combination with any other embodiment, the substrate is a zeolite. The co-feed can be present in amounts of from 0.1 to 5.0 wt % based on the total weight of the feed. The co-feed can remove at least a portion of the acid sites on the catalyst. The spatial volume near the acid sites of the catalyst can be occupied by molecules of the co-feed. In yet another embodiment, a process is provided for producing styrene including providing toluene, a co-feed, and a $C_1$ source to a reactor including a catalyst containing acid sites and reacting toluene with the $C_1$ source in the presence of the catalyst and the co-feed to form a product stream including ethylbenzene and styrene. The $C_1$ source is selected from the group of methanol, formaldehyde, formalin, trioxane, methylformcel, paraformaldehyde, methylal, dimethyl ether, and combinations thereof, and the co-feed is selected from the group of aniline, amines, cresol, anisol, and combinations thereof. The co-feed can be present in amounts from 0.1 to 5.0 wt % based on the total weight of the feed and removes at least a portion of the acid sites on the catalyst. Molecules of the co-feed can occupy spatial volume near acid sites of the catalyst, thereby rendering such acid sites as inactive.

The various embodiments of the present invention can be joined in combination with other embodiments of the invention and the listed embodiments herein are not meant to limit the invention. All combinations of embodiments of the invention are enabled, even if not given in a particular example herein.

BRIEF DESCRIPTION OF DRAWINGS

FIG. 2 illustrates a flow chart for the production of styrene by the reaction of formaldehyde and toluene, wherein methanol and toluene are fed into a reactor, wherein the methanol is converted to formaldehyde and the formaldehyde is reacted with toluene to produce styrene.

DETAILED DESCRIPTION

Figure 1:
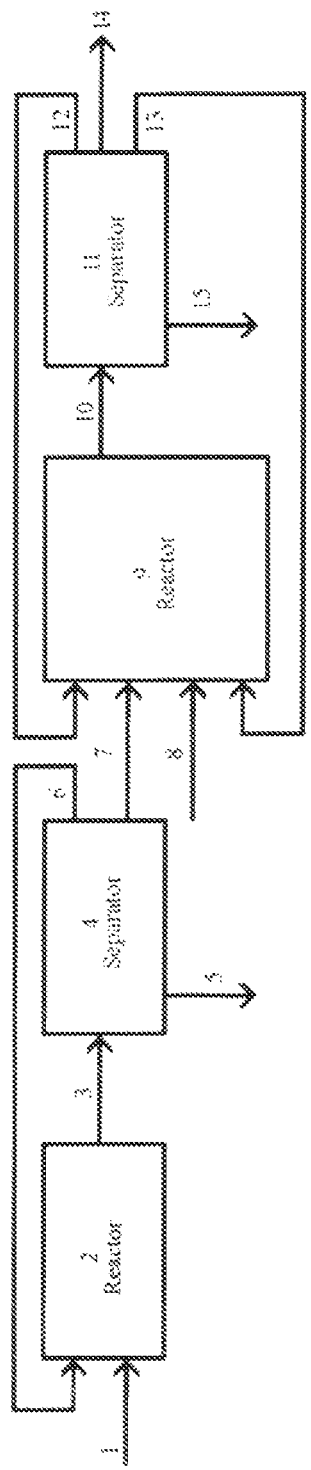
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene to produce styrene.

The present invention relates to increasing the activity and/or selectivity in an alkylation process, specifically an alkylation of toluene with methanol process. More specifically, the present invention is related to the modification of a catalyst, such as a zeolite catalyst, to reduce the number of acid sites on the catalyst. Also, the catalyst is modified by the addition of a molecule having a more basic character than that of toluene in a way that reduces the total number of acid sites of the zeolite catalyst, such that by-product formation is inhibited and styrene selectivity is increased. Also, the present invention includes the addition of a molecule having a steric character that would allow the molecule to occupy spatial volume near the acidic sites of the zeolite which can render such acid sites as inactive.

In accordance with an embodiment of the current invention, toluene is reacted with a carbon source, which can be referred to as a $C_1$ source, capable of coupling with toluene to produce styrene and ethylbenzene. In an embodiment, the $C_1$ source includes methanol or formaldehyde or a mixture of the two. In an alternative embodiment, toluene is reacted with one or more of the following: formalin (37-50% $H_2CO$ in solution of water and MeOH), trioxane (1,3,5-trioxane), methylformcel (55% $H_2CO$ in methanol), paraformaldehyde, methylal (dimethoxymethane), and dimethyl ether. In a further embodiment, the $C_1$ source is selected from the group of methanol, formaldehyde, formalin, trioxane, methylformcel, paraformaldehyde and methylal, dimethyl ether, and combinations thereof.

Formaldehyde can be produced either by the oxidation or dehydrogenation of methanol. In an embodiment, formaldehyde is produced by the dehydrogenation of methanol to produce formaldehyde and hydrogen gas. This reaction step produces a dry formaldehyde stream that may be preferred, as it would not require the separation of the water prior to the reaction of the formaldehyde with toluene. The dehydrogenation process is described in the equation below:

$$CH_3OH \rightarrow CH_2O + H_2$$

Formaldehyde can also be produced by the oxidation of methanol to produce formaldehyde and water. The oxidation of methanol is described in the equation below:

$$2CH_3OH + O_2 \rightarrow 2CH_2O + 2H_2O$$

In the case of using a separate process to obtain formaldehyde, a separation unit may then be used in order to separate the formaldehyde from the hydrogen gas or water from the formaldehyde and unreacted methanol prior to reacting the formaldehyde with toluene for the production of styrene. This separation would inhibit the hydrogenation of the formaldehyde back to methanol. Purified formaldehyde could then be sent to a styrene reactor and the unreacted methanol could be recycled.

Although the reaction has a 1:1 molar ratio of toluene and the $C_1$ source, the ratio of the C1 source and toluene feedstreams is not limited within the present invention and can vary depending on operating conditions and the efficiency of the reaction system. If excess toluene or $C_1$ source is fed to the reaction zone, the unreacted portion can be subsequently separated and recycled back into the process. In one embodiment the ratio of toluene:$C_1$ source can range from between 100:1 to 1:100. In alternate embodiments the ratio of toluene: $C_1$ source can range from 50:1 to 1:50; from 20:1 to 1:20; from 10:1 to 1:10; from 5:1 to 1:5; from 2:1 to 1:2. In a specific embodiment, the ratio of toluene:$C_1$ source can range from 2:1 to 5:1.

The acidity of zeolitic materials may present problems in catalytic performance, specifically in the alkylation of toluene with methanol and/or formaldehyde. The acidity, as well as the basicity, of the zeolitic material is dependent upon the amount of acid sites on the zeolitic material. The addition of a basic compound on or within or attached to the catalyst can increase the basic nature of the catalyst and reduce the effective acidity of the catalyst.

In an embodiment, the reactants, toluene and the C1 source, are combined with a co-feed having a basic property. In an embodiment, the co-feed is selected from basic compounds. In an embodiment, the co-feed is selected from the group of aniline, amines, cresol, anisol, and combinations thereof. The co-feed may be combined with the reactants in any desired amounts. In an embodiment, the co-feed is added in amounts ranging from 0.1 to 5.0 wt % based on the total weight of the feed. In another embodiment, the co-feed is added in amounts ranging from 0.25 to 2.5 wt % based on the total weight of the feed, optionally from 0.5 to 1.0 wt % based on the total weight of the feed.

Upon contact with the co-feed, at least a portion of the total number of acid sites on the zeolite may be selectively poisoned or masked by the co-feed. In an embodiment, the co-feed may have a more basic character than that of toluene. In an embodiment, the co-feed may have a steric character that may allow at least a portion of the co-feed to occupy spatial volume near the acid sites of the zeolite. In a further embodiment, the addition of the co-feed may alter the structural dimensions of the catalyst, resulting in the catalyst having an altered shape selectivity.

An improvement in side chain alkylation selectivity may be achieved by treating a molecular sieve zeolite catalyst with chemical compounds to inhibit the external acidic sites and to minimize aromatic alkylation on the ring positions. Another means of improvement of side chain alkylation selectivity can be to impose restrictions on the catalyst structure to facilitate side chain alkylation. In one embodiment the catalyst used in an embodiment of the present invention is a basic or neutral catalyst.

For the present invention, the catalyst can be a zeolite, but can also be a non-zeolite. A zeolite is generally a porous, crystalline alumino-silicate, and it can be formed either naturally or synthetically. One method of forming a synthetic zeolite is the hydrothermal digestion of silica, alumina, sodium or other alkyl metal oxide, and an organic templating agent. The amounts of each reactant and the inclusion of various metal oxides can lead to several different synthetic zeolite compositions. Furthermore, a zeolite is commonly altered through a variety of methods to adjust characteristics such as pore size, structure, activity, acidity, and silica/alumina molar ratio. Thus, a number of different forms of zeolite are available.

Zeolite materials suitable for this invention may include silicate-based zeolites and amorphous compounds such as faujasites, mordenites, etc. Silicate-based zeolites are made of alternating $SiO_4^{-4}$ and $MO_X$ tetrahedra, where M is an element selected from the Groups 1 through 16 of the Periodic Table (new IUPAC). These types of zeolites have 4, 6, 8, 10, or 12-membered oxygen ring channels. An example of the zeolites of the present invention can include faujasites, such as an X-type or Y-type zeolite and zeolite beta. Zeolite-like materials can also be an effective substrate. Alternate molecular sieves also contemplated are zeolite-like materials such as the crystalline silicoaluminophosphates (SAPO) and the aluminophosphates (ALPO) and the like.

Another method of altering a zeolite is by ion-exchange. For example, the hydrogen form of a zeolite can be produced by ion-exchanging beta zeolite with ammonium ions. Ion exchange may be performed by conventional ion exchange methods in which sodium, hydrogen, or other inorganic cations that may be typically present in a substrate are at least partially replaced via a fluid solution. In an embodiment, the fluid solution can include any medium that will solubilize the cation without adversely affecting the substrate. Increasing the amount of silica relative to alumina can have the effect of increasing the catalyst hydrophobicity.

In an embodiment, the ion exchange is performed by heating a solution containing any promoter selected from the group of Co, Mn, Ti, Zr, V, Nb, K, Cs, Ga, B, P, Rb, Ag, Na, Cu, Mg, Fe, Mo, Ce, and any combinations thereof in which the promoter(s) is(are) solubilized in the solution, which may be heated, and contacting the solution with the substrate. In another embodiment, the ion exchange includes heating a solution containing any one selected from the group of Ce, Cu, P, Cs, B, Co, Ga, and any combinations thereof. In an embodiment, the solution is heated to temperatures ranging from 50 to 120° C. In another embodiment, the solution is heated to temperatures ranging from 80 to 100° C.

A variety of zeolites and non-zeolites are available for use in the present invention. The various catalysts listed in this disclosure are not meant to be an exhaustive list, but is meant to indicate the type of catalysts for which may be useful in the present invention.

The catalytic reaction systems suitable for this invention can include one or more of the zeolite or amorphous materials modified for side chain alkylation selectivity. A non-limiting example can be a zeolite promoted with one or more metal ion of the following: Co, Mn, Ti, Zr, V, Nb, K, Cs, Ga, B, P, Rb, Ag, Na, Cu, Mg, Fe, Mo, Ce, and any combinations thereof. In general the promoter exchanges with Na within the zeolite or amorphous material. The promoter can also be attached to the zeolite or amorphous material in an occluded manner. In an embodiment the amount of promoter is determined by the amount needed to yield less than 0.5 mol % of ring alkylated products such as xylenes from a coupling reaction of toluene and a C1 source.

In an embodiment, the catalyst contains greater than 0.1 wt % of at least one promoter based on the total weight of the catalyst. In another embodiment, the catalyst contains up to 5 wt % of at least one promoter. In a further embodiment, the catalyst contains from 1 to 3 wt % of at least one promoter.

As used herein, the term "metal ion" is meant to include all active metal ions and similar species, such as metal oxides, nanoparticles, and mixed metal oxide phases, capable of being added to a catalyst, or to a binder and enabling the binder to reduce the acidity, or increase the basicity or basic strength, of the supported catalyst without adversely affecting the catalyst that it supports or causing significant by-product formation at reaction conditions.

The metal ion can be added to the zeolite, or non-zeolite, in the amount of 0.1% to 50%, optionally 0.1% to 20%, optionally 0.1% to 5%, by weight of the zeolite, or non-zeolite. The metal ion can be added to the zeolite, or non-zeolite, by any means known in the art. Generally, the method used is incipient wetness impregnation, wherein the metal ion precursor is added to an aqueous solution, which solution is poured over a zeolite. After sitting for a specified period, the zeolite is dried and calcined, such that the water is removed with the metal ion deposited on the surface of the zeolite. The ion-modified zeolite can then be mixed with a binder, or another catalyst, by any means known in the art. The mixture is shaped via extrusion or some other method into a form such as a pellet, tablet, cylinder, cloverleaf, dumbbell, symmetrical and asymmetrical polylobates, sphere, or any other shape suitable for the reaction bed. The shaped form is then usually dried and calcined. Drying can take place at a temperature of from 100° C. to 200° C. Calcining can take place at a temperature of from 400° C. to 900° C. in a substantially dry environment.

The powder form of a zeolite and other catalysts may be unsuitable for use in a reactor, due to a lack of mechanical stability, making alkylation and other desired reactions difficult. To render a catalyst suitable for the reactor, it can be combined with a binder to form an aggregate, such as a zeolite aggregate. The binder-modified zeolite, such as a zeolite aggregate, will have enhanced mechanical stability and strength over a zeolite that is not combined with a binder, or otherwise in powder form. The aggregate can then be shaped or extruded into a form suitable for the reaction bed. The binder can desirably withstand temperature and mechanical stress and ideally does not interfere with the reactants adsorbing to the catalyst. In fact, it is possible for the binder to form macropores, much greater in size than the pores of the catalyst, which provide improved diffusional access of the reactants to the catalyst.

Binder materials that are suitable for the present invention include, but are not limited to, silica, alumina, titania, zirconia, zinc oxide, magnesia, boria, silica-alumina, silica-magnesia, chromia-alumina, alumina-boria, silica-zirconia, silica gel, clays, kaolin, montmorillonite, modified clays, similar species, and any combinations thereof. The most frequently used binders are amorphous silica and alumina, including gamma-, eta-, and theta-alumina. It should be noted that a binder can be used with many different catalysts, including various forms of zeolite and non-zeolite catalysts that require mechanical support.

The reactants can enter the reactor via a single inlet or separate inlets. The reactants can be delivered to the reaction bed in the gaseous phase, the liquid phase, a combination of liquid and gaseous phase, the supercritical phase, or a combination of liquid and supercritical phases. The reaction conditions, including reactor type, pressure, temperature, liquid hourly space velocity (LHSV), and benzene to ethylene ratio depend in part on the phase in which the alkylation is to occur.

The operating conditions of the reactors and separators will be system specific and can vary depending on the feedstream composition and the composition of the product streams. The reactor for the reactions of methanol to formaldehyde and toluene with formaldehyde will operate at elevated temperatures and may contain a basic or neutral catalyst system. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

Inert diluents such as helium and nitrogen may be included in the feed to adjust the gas partial pressures. The reaction pressure is not a limiting factor regarding the present invention and any suitable condition is considered to be within the scope of the invention.

Any suitable space velocity, within the short reaction time parameters of the present invention, can be considered to be within the scope of the invention.

In FIG. 1 there is a simplified flow chart of one embodiment of the styrene production process described above. In this embodiment, a first reactor (2) is either a dehydrogenation reactor or an oxidation reactor. This reactor is designed to convert the first methanol feed (1) into formaldehyde. The gas product (3) of the reactor is then sent to a gas separation unit (4) where the formaldehyde is separated from any unreacted methanol and unwanted byproducts. Any unreacted methanol (6) can then be recycled back into the first reactor (2). The byproducts (5) are separated from the clean formaldehyde (7).

In one embodiment the first reactor (2) is a dehydrogenation reactor that produces formaldehyde and hydrogen and the separation unit (4) is a membrane capable of removing hydrogen from the product stream (3).

In an alternate embodiment the first reactor (2) is an oxidative reactor that produces product stream (3) comprising formaldehyde and water. The product stream (3) comprising formaldehyde and water can then be sent to the second reactor (9) without a separation unit (4).

The formaldehyde feed stream (7) is then reacted with a feed stream of toluene (8) and a co-feed stream (16) in a second reactor (9). The toluene and formaldehyde react to produce styrene. The product (10) of the second reactor (9) may then be sent to an optional separation unit (11) where any unwanted byproducts (15) such as water can separated from the styrene, unreacted formaldehyde and unreacted toluene. Any unreacted formaldehyde (12) and the unreacted toluene (13) can be recycled back into the reactor (9). A styrene product stream (14) can be removed from the separation unit (11) and subjected to further treatment or processing if desired.

The operating conditions of the reactors and separators will be system specific and can vary depending on the feedstream composition and the composition of the product streams. The reactor (9) for the reaction of toluene and formaldehyde will operate at elevated temperatures. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

FIG. 2 is a simplified flow chart of another embodiment of the styrene process discussed above. A $C_1$ source containing feed stream (21) is fed along with a feed stream of toluene (22) and a co-feed stream (31) in a reactor (23). Toluene and the $C_1$ source then react to produce styrene. The product (24) of the reactor (23) may then be sent to an optional separation unit (25) where any unwanted byproducts (26) can be separated from the styrene, and any unreacted C1 source, unreacted methanol, unreacted formaldehyde and unreacted toluene. Any unreacted methanol (27), unreacted formaldehyde (28) and the unreacted toluene (29) can be recycled back into the reactor (23). A styrene product stream (30) can be removed from the separation unit (25) and subjected to further treatment or processing if desired.

The operating conditions of the reactors and separators will be system specific and can vary depending on the feedstream composition and the composition of the product streams. The reactor (23) for the reactions of methanol to formaldehyde and toluene with formaldehyde will operate at elevated temperatures. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

Upon deactivation, the zeolite may require a regeneration procedure to be performed. Some methods of regenerating a zeolite include heating to remove adsorbed materials, ion exchanging with sodium to remove unwanted cations, or a pressure swing to remove adsorbed gases. One solution involves flushing the catalyst with benzene. Other solutions generally involve processing the catalyst at high temperatures using regeneration gas and oxygen. According to one procedure, a zeolite beta can be regenerated by heating the catalyst first to a temperature in excess of 300° C. in an oxygen-free environment. Then an oxidative regeneration gas can be supplied to the catalyst bed with oxidation of a portion of a relatively porous coke component to produce an exotherm moving through the catalyst bed. Either the temperature or the oxygen content of the gas can be progressively increased to oxidize a porous component of the coke. Again, regeneration gas can be supplied, wherein the gas has either increased oxygen content or increased temperature to oxidize a less porous refractory component of the coke. The regeneration process can be completed by passing an inert gas through the catalyst bed at a reduced temperature.

In one embodiment, the present invention is for an alkylation process containing a catalyst, wherein toluene, a C1 source, and a co-feed are fed to a reactor containing the catalyst wherein the co-feed removes at least a portion of the total number of acid sites on the catalyst. In another embodiment, the present invention is for an alkylation process containing a catalyst, wherein toluene, a C1 source, and a co-feed are fed to a reactor containing the catalyst wherein the co-feed adds basic sites to the catalyst. In yet another embodiment, the present invention is for an alkylation process containing a catalyst, wherein toluene, a C1 source, and a co-feed are fed to a reactor containing the catalyst wherein the molecules of the co-feed can occupy spatial volume near the acidic sites of the zeolite.

EXAMPLES

A catalyst promoted with both Cs and B was used in an ATM reaction with the addition of triethylamine in amounts of 0 ppm, 500 ppm, and 1000 ppm. The reactions each had a Tolene:MeOH ratio of 1.0, a LHSV of 1.5 $hr^{-1}$, and temperature of 420° C., pressure of 1.3 psig and a 2.5 second contact time. The results are shown in Table 1.

The addition of triethylamine increased the toluene conversion and did not decrease styrene selectivity. The addition of 500 ppm triethylamine increased toluene conversion by about 15% without an increase in methanol conversion. With 1000 ppm triethylamine the toluene conversion increased by about 20% and did not indicate a reduction in toluene conversion throughout the run thereby giving a reduced deactivation rate. The methanol conversion increased at the 1000 ppm triethylamine. The cumene and alpha methyl styrene remained low and within acceptable ranges.

TABLE 1

| Triethylamine (ppm) | Time On Stream (hh:mm) | $X_{Tol}$ | $S_{Bz}$ | $S_{Xyl}$ | $S_{EB}$ | $S_{Sty}$ | $S_{Cumene}$ | $S_{ams}$ | $X_{MeOH}$ |
|---|---|---|---|---|---|---|---|---|---|
| None | 1:44 | 9.7 | 0.7 | 0.140 | 76.5 | 20.4 | 1.80 | 0.4 | 48.9 |
|  | 2:10 | 9.6 | 0.7 | 0.144 | 75.3 | 21.7 | 1.76 | 0.4 | 45.3 |
|  | 2:46 | 9.5 | 0.7 | 0.151 | 75.0 | 22.0 | 1.73 | 0.4 | 48.0 |
|  | 4:09 | 10.0 | 0.5 | 0.158 | 73.9 | 22.1 | 2.49 | 0.6 | 46.0 |
|  | 5:13 | 8.3 | 0.5 | 0.214 | 74.8 | 21.1 | 2.52 | 0.5 | 48.6 |
| 500 | 1:11 | 11.8 | 0.9 | 0.928 | 73.8 | 20.7 | 2.42 | 0.6 | 50.2 |
|  | 1:44 | 12.2 | 0.6 | 0.667 | 74.2 | 21.0 | 2.41 | 0.6 | 48.3 |
|  | 2:14 | 12.3 | 0.7 | 0.535 | 74.3 | 21.0 | 2.35 | 0.6 | 61.7 |
|  | 2:49 | 12.2 | 0.9 | 0.475 | 73.4 | 21.5 | 2.47 | 0.7 | 30.4 |
|  | 4:21 | 7.0 | 0.7 | 0.220 | 77.7 | 19.9 | 1.19 | 0.2 | 43.3 |
|  | 5:21 | 6.4 | 0.7 | 0.238 | 78.2 | 19.4 | 1.20 | 0.2 | 41.2 |
| 1000 | 1:05 | 12.0 | 0.8 | 0.142 | 77.3 | 19.5 | 1.99 | 0.3 | 70.2 |
|  | 1:44 | 12.3 | 0.6 | 0.147 | 75.6 | 20.8 | 2.17 | 0.4 | 74.5 |
|  | 2:17 | 12.5 | 0.6 | 0.148 | 75.6 | 20.9 | 2.14 | 0.4 | 63.5 |
|  | 2:56 | 11.6 | 0.6 | 0.162 | 74.1 | 22.2 | 2.21 | 0.4 | 69.6 |
|  | 4:01 | 12.1 | 0.5 | 0.183 | 73.6 | 22.5 | 2.33 | 0.5 | 59.6 |
|  | 5:03 | 12.2 | 0.4 | 0.201 | 72.8 | 23.1 | 2.37 | 0.6 | 58.4 |

Procedure used to produce the cesium ion-exchanged zeolite material: A glass cylinder (2" inside diameter), fitted with a sintered glass disk and stopcock at the lower end, was charged with 544-HP zeolite (100 g, W.R. Grace) and CsOH (400 mL, 1.0 M in water). The mixture was then brought to 90° C. and allowed to stand for 4 h. The liquid was drained from the zeolite material and another aliquot of CsOH (400 mL of 1.0 M solution in water) was added and allowed to stand for 3 hours at 90° C. The liquid was drained from the zeolite material and another aliquot of CsOH (400 mL of 1.0 M solution in water) was added and allowed to stand for 15 hours at 90° C. The liquid was drained from the zeolite material and dried at 150° C. for 1.5 hours.

Deposition of 1.4 wt % boron onto cesium ion-exchanged zeolite material: The cesium ion-exchanged zeolite material (35 g) was treated with a solution of boric acid (2.8 g) dissolved in acetone (500 mL) at room temperature for 2 hours. The (Cs,B)/X material was then dried at 110° C. for 20 hours.

The term "conversion" refers to the percentage of reactant (e.g. toluene) that undergoes a chemical reaction.

$X_{Tol}$=conversion of toluene (mol %)=(Tol$_{in}$−Tol$_{out}$)/Tol$_{in}$ $X_{MeOH}$=conversion of methanol to styrene+ethylbenzene (mol %)

The term "molecular sieve" refers to a material having a fixed, open-network structure, usually crystalline, which may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

The term "selectivity" refers to the relative activity of a catalyst in reference to a particular compound in a mixture. Selectivity is quantified as the proportion of a particular product relative to all other products.

$S_{Sty}$=selectivity of toluene to styrene (mol %)=Sty$_{out}$/Tol$_{converted}$ $S_{Bz}$=selectivity of toluene to benzene (mol %)=Benzene$_{out}$/Tol$_{converted}$ $S_{EB}$=selectivity of toluene to ethylbenzene (mol %)=EB$_{out}$/Tol$_{converted}$ $S_{Xyl}$=selectivity of toluene to xylenes (mol %)=Xylenes$_{out}$/Tol$_{converted}$ $S_{Sty+EB}$(MeOH)=selectivity of methanol to styrene+ethylbenzene (mol %)=(Sty$_{out}$+EB$_{out}$)/MeOH$_{converted}$ The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

The various embodiments of the present invention can be joined in combination with other embodiments of the invention and the listed embodiments herein are not meant to limit the invention. All combinations of various embodiments of the invention are enabled, even if not given in a particular example herein.

While illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Also, it is within the scope of this disclosure that the embodiments disclosed herein are usable and combinable with every other embodiment disclosed herein, and consequently, this disclosure is enabling for any and all combinations of the embodiments disclosed herein. Other and further embodiments, versions and examples of the invention may be devised without departing from the basic scope thereof and the scope thereof is determined by the claims that follow.

What is claimed is:

1. A process for making styrene comprising:
   providing toluene, a co-feed, and a C1 source to a reactor comprising a catalyst containing acid sites; wherein the catalyst comprises a X-zeolite and Cs; and
   reacting toluene with the C1 source in the presence of the catalyst and the co-feed to form a product stream comprising ethylbenzene and styrene;
   wherein the C1 source is selected from the group consisting of methanol, formaldehyde, formalin, trioxane, methylformcel, paraformaldehyde, methylal, dimethyl ether, and combinations thereof;
   wherein the co-feed is a base compound that reduces the number of active acid sites on the catalyst; wherein the co-feed is selected from the group consisting of aniline, cresol, anisol, and combinations thereof.

2. The process of claim 1, wherein the co-feed adds basic sites to the catalyst.

3. The process of claim 1, wherein the co-feed reduces at least a portion of the active acid sites on the catalyst by the molecules of the co-feed occupying spatial volume near the acid sites of the catalyst.

4. The process of claim 1, wherein the co-feed is added to the catalyst prior to the toluene and the $C_1$ source.

5. The process of claim 1, wherein the co-feed is simultaneously fed to the reactor with the toluene and the $C_1$ source.

6. The process of claim 1, wherein the co-feed is present in amounts of from 0.1 to 5.0 wt % based on the total weight of the feed.

7. The process of claim 1, wherein co-feed is present in amounts of from 0.5 to 1.0 wt % based on the total weight of the feed.

8. The process of claim 1, comprising a toluene conversion of at least 3 mol %.

9. The process of claim 1, comprising a selectivity to styrene of at least 10 mol %.

10. The process of claim 1, comprising a selectivity to ethylbenzene of at least 10 mol %.

11. A process of producing styrene comprising:
    providing toluene, a co-feed, and a $C_1$ source to a reactor comprising a catalyst containing acid sites; wherein the catalyst comprises a X-zeolite and Cs has been inserted; and
    reacting toluene with the $C_1$ source in the presence of the catalyst and the co-feed to form a product stream comprising ethylbenzene and styrene;
    wherein the $C_1$ source is selected from the group consisting of methanol, formaldehyde, formalin, trioxane, methylformcel, paraformaldehyde, methylal, dimethyl ether, and combinations thereof;
    wherein the co-feed is selected from the group consisting of aniline, cresol, and anisol, and combinations thereof;
    wherein the co-feed is present in amounts from 0.1 to 5.0 wt % based on the total weight of the feed and removes at least a portion of the acid sites on the catalyst; and
    wherein molecules of the co-feed can occupy spatial volume near the acid sites of the catalyst.

\* \* \* \* \*